United States Patent [19]

Bahn

[11] Patent Number: 5,509,412
[45] Date of Patent: Apr. 23, 1996

[54] MAGNETIC RESONANCE IMAGING OF BLOOD VOLUME

[75] Inventor: Mark M. Bahn, Creve Coeur, Mo.

[73] Assignee: Wisconsin Alumni Research Foundation, Madison, Wis.

[21] Appl. No.: 295,190

[22] Filed: Aug. 24, 1994

[51] Int. Cl.$^6$ .................................................. A61B 5/005
[52] U.S. Cl. ...................... 128/653.2; 324/306; 324/309; 128/653.3; 128/653.4
[58] Field of Search ............................... 128/653.2, 653.3, 128/653.4, 654; 324/306, 309

[56] References Cited

U.S. PATENT DOCUMENTS

| | | | |
|---|---|---|---|
| 5,190,744 | 3/1993 | Rocklage et al. | 324/306 |
| 5,352,979 | 10/1994 | Conturo | 324/307 |
| 5,363,042 | 11/1994 | Dumoulin | 324/306 |
| 5,408,180 | 4/1995 | Mistretta et al. | 324/306 |

OTHER PUBLICATIONS

Nonlinear Models, *Numerical Recipes in C*, 1992, pp. 681–688, W. H. Press, et al.

Tumor Vascularity in the Brain: Evaluation with Dynamic Susceptibility–Contrast MR Imaging[1,] *Radiology* 1993; 189:233–238, M. Maeda, et al.

Susceptibility Contrast Imaging of Cerebral Blood Volume: Human Experience, *Magnetic Resonance in Medicine* 22, 293–299 (1991), B. R. Rosen, et al.

Perfusion Imaging with NMR Contrast Agents, *Magnetic Resonance in Medicine* 14, 249–165 (1990) B. R. Rosen et al.

Functional Cerebral Imaging by Susceptibility–Contrast NMR, *Magnetic Resonance in Medicine* 14, 538–546 (1990), J. W. Belliveau, et al.

Contrast Agents and Cerebral Hemodynamics, *Magnetic Resonance in Medicine* 19, 285–292 (1991), B. R. Rosen, et al.

Functional Studies of the Human Brain Using High–Speed Magnetic Resonance Imaging, *Journal of Neuroimaging* vol. 1, No. 1, pp. 36–41, Feb. 1991, J. W. Belliveau, et al.

Advances in Clinical Neuroimaging: Functional MR Imaging Techniques, *RadioGraphics*, vol. 13, No. 4, Jul. 1993, pp. 889–896, B. R. Rosen et al.

Perfusion Imaging by Nuclear Magnetic Resonance, *Magnetic Resonance Quarterly*, vol. 5, No. 4, pp. 263–281, 1989, B. R. Rosen, et al.

Dynamic Imaging with Lanthanide Chelates in Normal Brain: Contrast Due to Magnetic Susceptibility Effects, *Magnetic Resonance in Medicine*, 6, 164–174 (1988), A. Villringer, et al.

MR Contrast Due to Microscopically Heterogeneous Magnetic Susceptibility: Numerical Simulations and Applications to Cerebral Physiology, *Magnetic Resonance in Medicine* 17, 336–347 (1991), C. R. Fisel, et al.

Perfusionl Diffusion Quantitation with Magnetic Resonance Imaging, *Investigative Radiology*, Dec. Supplement 1992, pp. S12–S17, D. R. Pickens.

Cerebral Blood Flow Determination by Rapid–Sequence Computed Tomography, *Neuroradiology*, Dec. 1980, 679–686, L. Axel.

Cerebral Transit of an Intravascular Tracer May Allow Measurement of Regional Blood Volume But Not Regional Blood Flow, *Journal of Cerebral Blood Flow & Metabolism* 4:633–634 1984.

Indicator Transit Time Considered as a Gamma Variate, *Circulation Research*, vol. XIV, pp. 502–515, Jun. 1964, H. K. Thompson, et al.

Primary Examiner—Krista M. Zele
Assistant Examiner—Brian L. Casler
Attorney, Agent, or Firm—Quarles & Brady

[57] ABSTRACT

An MRI system acquires a series of images over a course of time using an echo planar imaging pulse sequence. A susceptibility contrast agent is injected into the subject during the scan to momentarily reduce NMR signal strength from voxels with blood flow. A nonlinear regression parameter estimation process is employed to calculate blood volume at each voxel directly from the acquired NMR data.

5 Claims, 4 Drawing Sheets

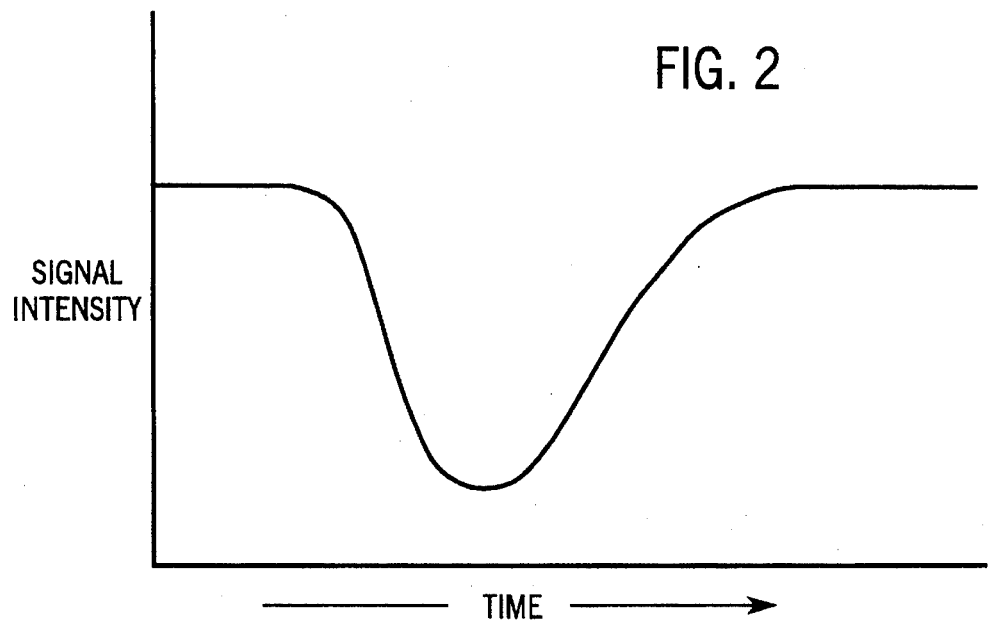
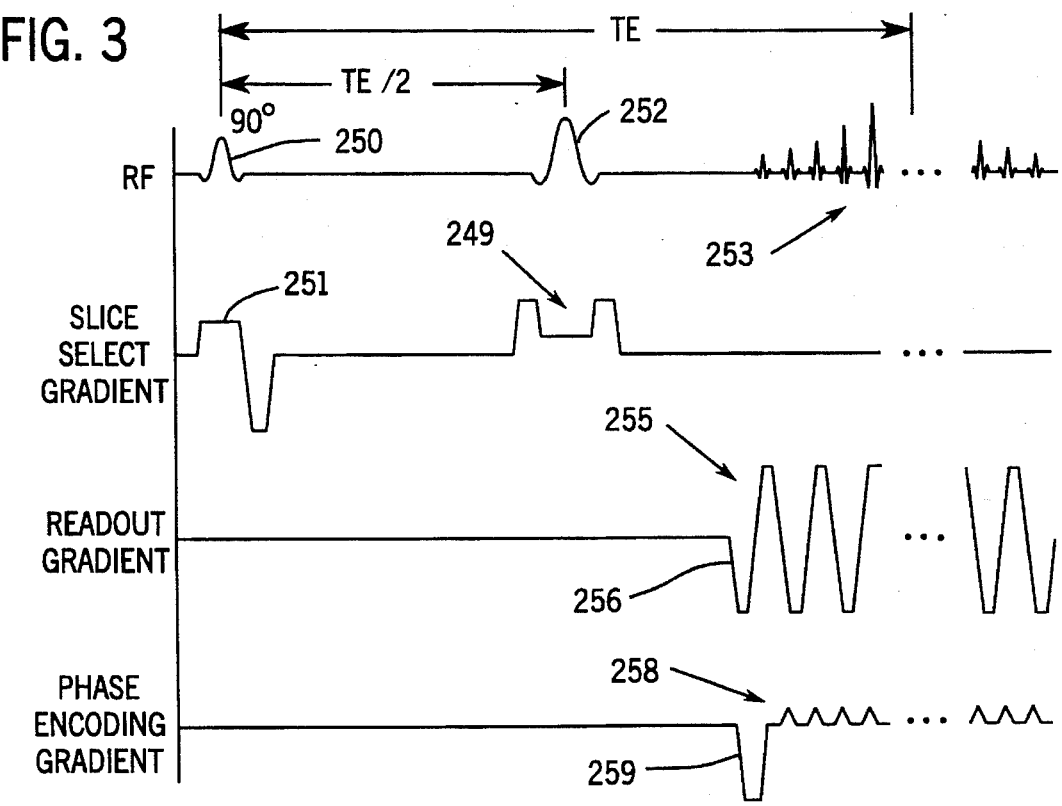

MAGNETIC RESONANCE IMAGING OF BLOOD VOLUME

BACKGROUND OF THE INVENTION

The field of the invention is nuclear magnetic resonance imaging methods and systems. More particularly, the invention relates to the production of MRI images based on the measurement of blood volume.

When a substance such as human tissue is subjected to a uniform magnetic field (polarizing field B0), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$ and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

The NMR signal which is emitted by tissue after excitation decays in amplitude at a characteristic rate referred to as the $T_2$ relaxation rate. The $T_2$ relaxation rate of a tissue is determined by a number of factors, including its magnetic susceptibility. There are many NMR pulse sequences which are particularly sensitive to differences in the $T_2$ relaxation rate of tissues, and these are employed to produce images in which the contrast between these tissues is enhanced. For example, the $T_2$ time of cerebral fluid is significantly different than that of gray matter and excellent MRI images of the brain can be obtained with $T_2$ weighted MRI scans.

While conventional $T_2$ weighted images of the brain will often differentiate tumors from normal brain tissues, they do not provide sufficient clinical information. For example, such images do not differentiate between benign and malignant tissue, or between radiation necrosis and tumor recurrence, or (in a malignant tumor containing heterogeneous tissue types) between low grade and high grade malignant tissues. As a result, other imaging modalities such as x-ray angiography, positron emission tomography (PET) or single-photon emission computed tomography (SPECT) have been used to obtain the additional clinical information needed to diagnose and treat brain tumors.

Recently, dynamic susceptibility contrast MRI methods have been developed to study brain functions and to assess tumor vascularity. These methods employ a magnetic susceptibility contrast agent which is injected into the patient's vasculature during the acquisition of a series of MRI images of the brain. A reduction in NMR signal intensity occurs when the susceptibility contrast agent flows into image voxels. The overall decrease in signal intensity within each voxel as the "bolus" of susceptibility contrast agent flows through the brain is a measure of the blood volume within each voxel. An image based on these blood volume measurements thus contrasts those regions of the brain which contain different proportions of blood per unit volume and provides valuable clinical information regarding brain tissue health.

The quality of the image produced using dynamic susceptibility contrast methods is determined largely by the accuracy with which blood volume in each voxel can be estimated. Since the NMR signals themselves are very small relative to system noise, and the "dip" in amplitude due to the susceptibility contrast agent is even smaller, the results achieved by simply integrating the measured dip over the time interval in which the bolus passes does not produce an accurate result. Also, although the values that would be produced for each voxel by integrating the image intensities over time may be in some sense qualitatively similar to the cerebral blood volume, they would not be quantitatively proportional to the cerebral blood volume in each voxel. In addition, the results can be adversely affected by recirculation of the susceptibility contrast agent through the voxels while contrast from the initial bolus is still present.

SUMMARY OF THE INVENTION

The present invention is a method for producing an MR image based on an estimation of blood volume in each image voxel during a scan in which a bolus of susceptibility contrast agent is injected into the patient and a time course set of NMR image data is acquired. More specifically, the method includes: injecting a patient with a susceptibility contrast agent; acquiring NMR image data from the stationary patient as the susceptibility contrast agent flows through the voxels from which the NMR image data is acquired; reconstructing a set of NMR images in which the intensity values $S_{xy}(t)$ indicate the NMR signal level at each voxel at a corresponding set of times during which the susceptibility contrast agent flows through the voxel; calculating a blood volume value (BV) at each voxel by fitting a model curve that includes as one of its defining parameters the blood volume value (BV) to the set of intensity values $S_{xy}(t)$ for the voxel using a nonlinear regression; and producing an image in which the intensity of each voxel is indicated by its blood volume value (BV).

It has been discovered that the measured intensity values $S_{xy}(t)$ can be fit to a model curve that includes as one of its defining parameters the blood volume value BV. Using a nonlinear regression method, the defining parameters of this curve, including the blood volume value (BV), are adjusted until the best fit with the measured values $S_{xy}(t)$ is achieved.

A more specific object of the invention is to enhance the accuracy and speed at which the blood volume value BV is calculated using the nonlinear regression method. The measured values $S_{xy}(t)$ are employed to provide seed values for many of the parameters that are adjusted during the nonlinear regression. These seed values are employed during the first iteration and insure that the nonlinear regression converges quickly to the most accurate fit in a few iterations.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

BRIEF DESCRIPTION OF THE DRAWINGS

FIG. 2 is a graphic representation of NMR signal intensity as a function of time in a voxel through which a bolus of susceptibility contrast agent flows (the effects of recirculation of contrast agent are not shown);

FIG. 3 is a graphic representation of the EPI spin echo pulse sequence employed in the preferred embodiment of the invention;

GENERAL DESCRIPTION OF THE INVENTION

Figure 1:
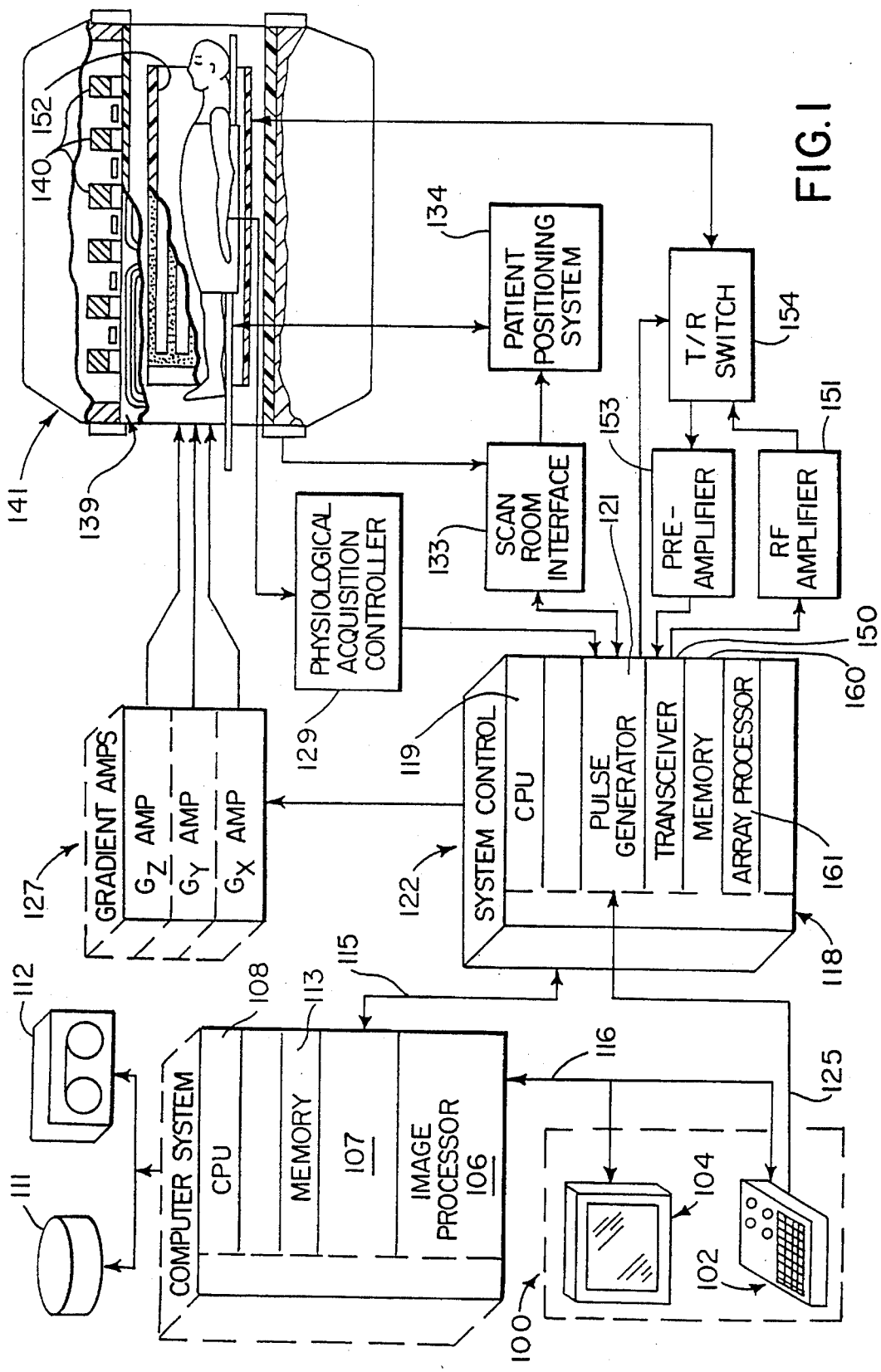
FIG. 1 is a block diagram of an MRI system which employs the present invention.

To measure blood volume through each image voxel a series of MR images are acquired using a $T_2$ or $T_2^*$ weighted pulse sequence. Each reconstructed image indicates the intensity, (S) of the NMR signal at a particular voxel (x,y) and at a particular time (t). The set of intensity values $S_{xy}(t)$ for a particular voxel over the entire acquisition time are employed to calculate the blood volume BV for that particular voxel. The process is repeated for each voxel (x,y) to produce a corresponding set of blood volume values $BV_{xy}(t)$ from which the final image is produced.

The relationship between the measured signal value $S_{xy}(t)$ and the concentration of susceptibility contrast agent in the voxel $C_{xy}(t)$ is given by the following equation:

$$C_{xy}(t) = \frac{-1}{kTE} \log_e \frac{S_{xy}(t)}{S_0} \quad (1)$$

where:

k=proportionality constant

TE=echo time of the pulse sequence used $S_0$=signal value before susceptibility contrast agent passes through voxel.

The blood volume in a voxel can be estimated by integrating the concentration values $C_{xy}(t)$ over the time interval during which the bolus of contrast agent passes through the voxel. However, because the acquired data will invariably include the effects produced by recirculated contrast agent, the data must first be filtered. This is accomplished by assuming that the concentration-versus-time curve during the transit of a single bolus of susceptibility contrast agent will follow a gamma variate function illustrated in FIG. 2, and defined by the following equation:

$$C_{xy}(t) = C_{peak} \left( \frac{e}{\alpha\beta} \right)^\alpha (t - T_a)^\alpha \exp\left( \frac{-(t - T_a)}{\beta} \right) \quad (2)$$

where e is the transcendental number (approximately 2.71828). The parameters of this gamma variate function are: alpha ($\alpha$), beta ($\beta$), peak concentration of the contrast agent ($C_{peak}$), and arrival time of the contrast value ($T_a$). Unlike the other two parameters of the gamma variate function, alpha and beta do not have simple physical interpretations. Alpha influences the initial increase in $C_{xy}(t)$ through the power term $(t-T_a)^\alpha$. The negative exponential term which involves beta, $\exp(-(t-T_a)/\beta)$, eventually dominates the equation and returns $C_{xy}(t)$ to zero. The constant term $(e/\alpha\beta)^\alpha$ influences the area under the curve. Fitting the measured concentration values to this gamma variate model enables the concentration curve to be extrapolated in time without the inaccuracies produced by recirculation of the blood.

Blood volume can be estimated by calculating the area under the concentration curve $C_{xy}(t)$:

$$BV_{xy} = \int_0^\infty C_{xy}(t)dt = C_{peak} \left( \frac{e}{\alpha\beta} \right)^\alpha \beta^{(\alpha+1)} \Gamma(\alpha + 1) \quad (3)$$

where: $\Gamma$=is the gamma function, the continuous extension of the well known factorial function.

Rather than calculating blood volume (BV) in a three step process using the above equations 1–3, the present invention calculates blood volume (BV) directly from the acquired NMR signal intensity values $S_{xy}(t)$.

This is accomplished by combining equation (2) describing the gamma variate function with equation (1) for converting scan values to concentration values. The resulting composite function is as follows:

$$S_{xy}(t) = S_0 \exp\left\{ -k\, TE\, C_{peak} \left( \frac{e}{\alpha\beta} \right)^\alpha (t - T_a)^\alpha \exp\left( \frac{-(t - T_a)}{\beta} \right) \right\}. \quad (4)$$

In this function the baseline NMR signal intensity value $S_0$ is a fitted parameter. All of the NMR signal values therefore contribute to the estimation of $S_0$ instead of only $S(0)$ or the first few values of $S_{xy}(t)$. This minimizes the propagation of errors which would occur if a poor estimate of $S_0$ were used in equation (1) for the conversion of the scan intensity values into concentration values.

Finally, equation (4) is reparameterized so that the area under the gamma variate curve (proportional to BV) is fitted directly as a model parameter. Substitution of equation (5) into equation (4) produces equation (6) which directly relates the scan values to area under the fitted gamma variate curve, i.e. to BV.

$$C_{peak} = \frac{BV}{\Gamma(\alpha+1)} \left( \frac{e}{\alpha\beta} \right)^{-\alpha} \beta^{-(\alpha+1)} \quad (5)$$

$$S_{xy}(t) = S_0 \exp\left\{ \frac{-k\, TE\, BV}{\Gamma(\alpha+1)} \beta^{-(\alpha+1)} (t - T_a)^\alpha \exp\left( \frac{-(t - T_a)}{\beta} \right) \right\}. \quad (6)$$

A nonlinear regression method is employed to estimate the parameters in equation (6) to best fit it with the time course NMR signal intensity values $S_{xy}(t)$. The blood volume parameter (BY) is thus calculated directly from the acquired NMR signal values in a single step process.

As described in Chapter 15 of *"Numerical Recipes in C, The Art of Scientific Computing Second Edition"*, W. H. Press, S. A. Teukolsky, W. T. Vetterling, B. P. Flannery, published in 1992 by Cambridge University Press, the nonlinear regression method uses values of the partial derivative of $S_{xy}(t)$ (in equation 6) with respect to all of its parameters; $\alpha$, $\beta$, BV, $T_a$ and $S_0$ at various times. These partial derivatives can be estimated numerically, but this would compromise speed and accuracy. The preferred implementation of the nonlinear regression process requires knowledge of the analytical forms of these partial derivatives. These are supplied in Appendix A. The partial derivative with respect to the parameter $\alpha$ involves the derivative of $\Gamma(\alpha+1)$. This results in an expression containing a Digamma or Psi function. An accurate and rapid numerical method of evaluating the Digamma or Psi function is described in Appendix B.

DESCRIPTION OF THE PREFERRED EMBODIMENT

Referring first to FIG. 1, there is shown the major components of a preferred MRI system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a ICPU module 108 and a memory module 113, known in the art as a frame buffer for storing image data arrays. The computer system 107 is linked to a disk storage 111 and a tape drive 112 for storage of image data and programs, and it communicates with a separate system control 112 through a high speed serial link 115.

The system control 122 includes a set of modules connected together by a backplane 118. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiclogical acquisition controller 129 that receives signals from a number of different sensors connected to the patient, such as ECG signals from electrodes or respiratory signals from a bellows. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil) to be used in either the transmit or receive mode.

The NMR signals picked up by the RF coil 152 are digitized by the transceiver module 150 and transferred to a memory module 160 in the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 as will be described in more detail below, and conveyed to the operator console 100 and presented on the display 104.

The EPI pulse sequence employed in the preferred embodiment of the invention is illustrated in FIG. 3. A 90° RF excitation pulse 250 is applied in the presence of a $G_z$ slice select gradient pulse 251 to produce transverse magnetization in a slice through the brain 7 mm thick. At time TE/2 a selective 180° RF excitation pulse 252 is applied in the presence of a $G_z$ slice select gradient pulse 249, and a short time interval later the readout sequence begins. A total of 128 separate NMR echo signals, indicated generally at 253, are acquired during the EPI pulse sequence. Each NMR echo signal 253 is a different view which is separately phase encoded to scan $k_y$-space from $k_y = -64$ to $k_y=+64$ in monotonic order. The readout sequence is positioned such that the view acquired at $k_y=0$ occurs at the desired echo time (TE). While echo times may range from TE=20 to 120 ms, in brain studies the best images have been obtained with echo times of approximately 100 ms.

The NMR echo signals 253 are echo's produced by the application of an oscillating $G_x$ readout gradient field 255. The readout sequence is started with a negative readout gradient lobe 256 and the echo signals 253 are produced as the readout gradient oscillates between positive and negative values. A total of 256 samples are taken of each NMR echo signal during each readout gradient pulse 255. The successive 128 NMR echo signals 253 are separately phase encoded by a series of $G_y$ phase encoding gradient pulses 258. The first pulse is a negative lobe 259 that occurs before the echo signals are acquired to encode the first view at $k_y=-64$. Subsequent phase encoding pulses 258 occur as the readout gradient pulses 255 switch polarity, and they step the phase encoding monotonically upward through $k_y$ space.

At the completion of the EPI pulse sequence, therefore, 256 separate frequency encoded samples of 128 separately phase encoded NMR echo signals 253 have been acquired. This acquired NMR data is used to reconstruct a 256×128 pixel image by performing a two-dimensional Fourier transform first along the readout axis and then along the phase encoding axis. The reconstructed image is stored in the disc memory 111 as described above. In the preferred embodiment this EPI pulse sequence is repeated to acquire eight images at successive slice locations along the z axis. The 7 mm slices are spaced apart 1 mm.

Figure 4:
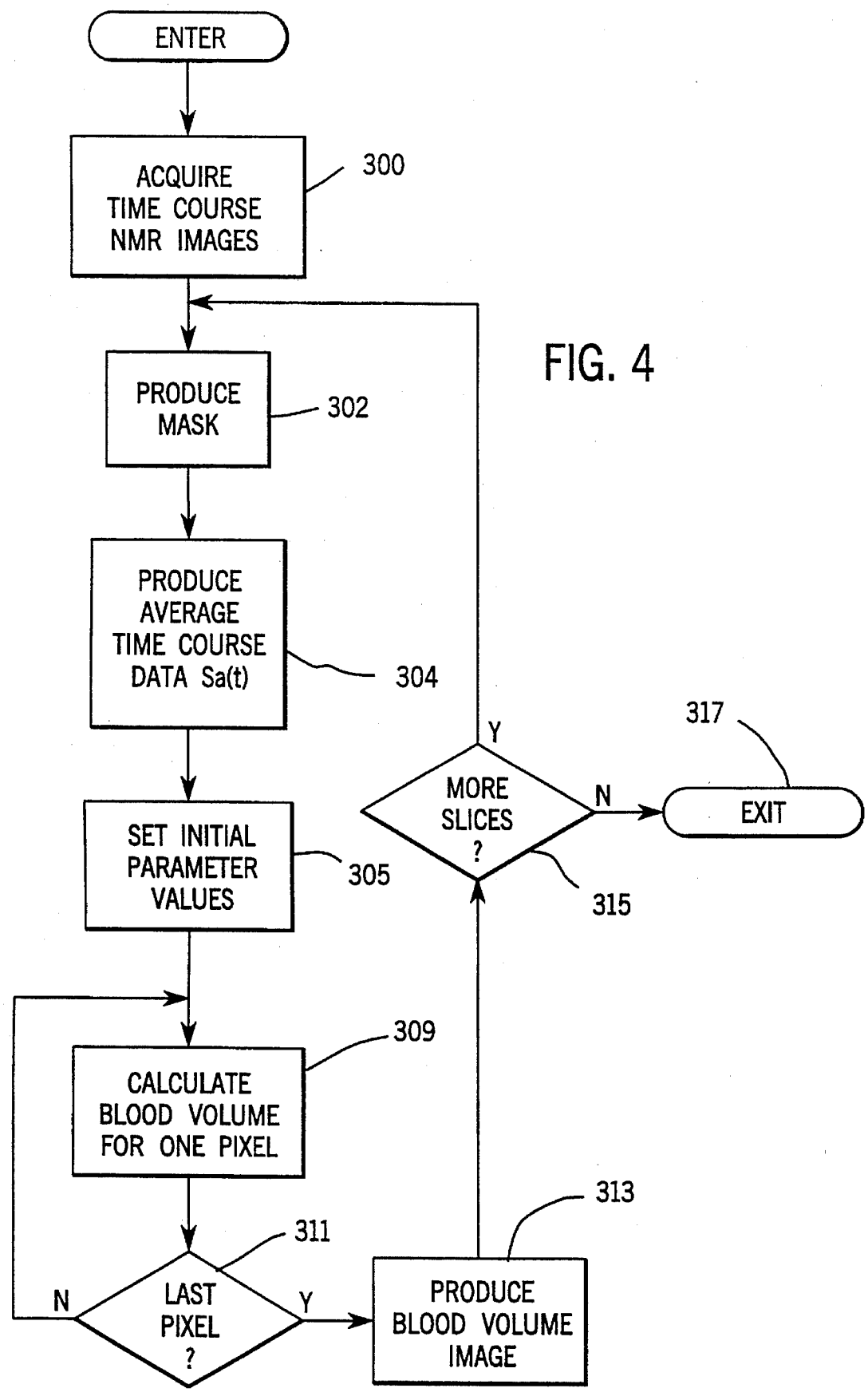
FIG. 4 is a flow chart of the program employed in the MRI system of FIG. 1 to practice the preferred embodiment of the invention.

Referring particularly to FIG. 4, the preferred embodiment of the invention is performed under the direction of a program executed by the computer system 107. As indicated by process block 300, the first step is to acquire a set of time course NMR images using the EPI pulse sequence described above. A total of 64 time course NMR images are acquired at 1.5 second intervals for each of the eight slice locations. The patient is injected with a "bolus" of susceptibility contrast agent such as gadolinium or dysprosium immediately after the start of the data acquisition, and the approximately 96 seconds over which the time course NMR data is acquired is sufficiently long to allow the bolus to flow to all parts of the patient's anatomy. The 64 time course NMR images record the NMR signal levels before the contrast agent reaches the anatomy being imaged, and it records the dip in the NMR signal levels as the bolus transits the imaged slice.

Figure 5:
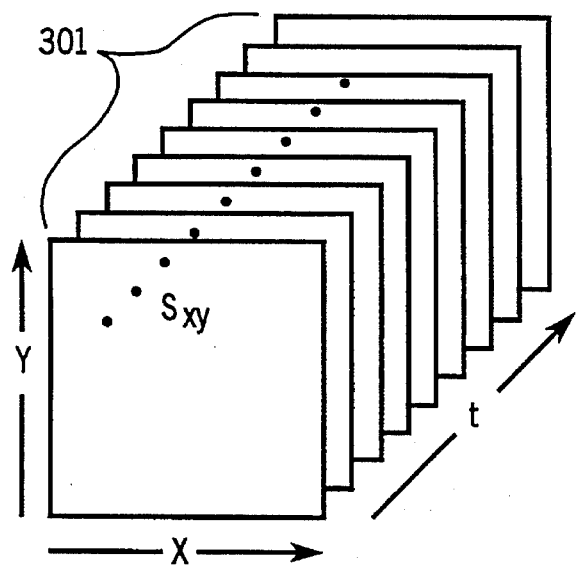
FIG. 5 is a pictorial representation of the set of NMR image data acquired with the pulse sequence of FIG. 3.
Figure 6:
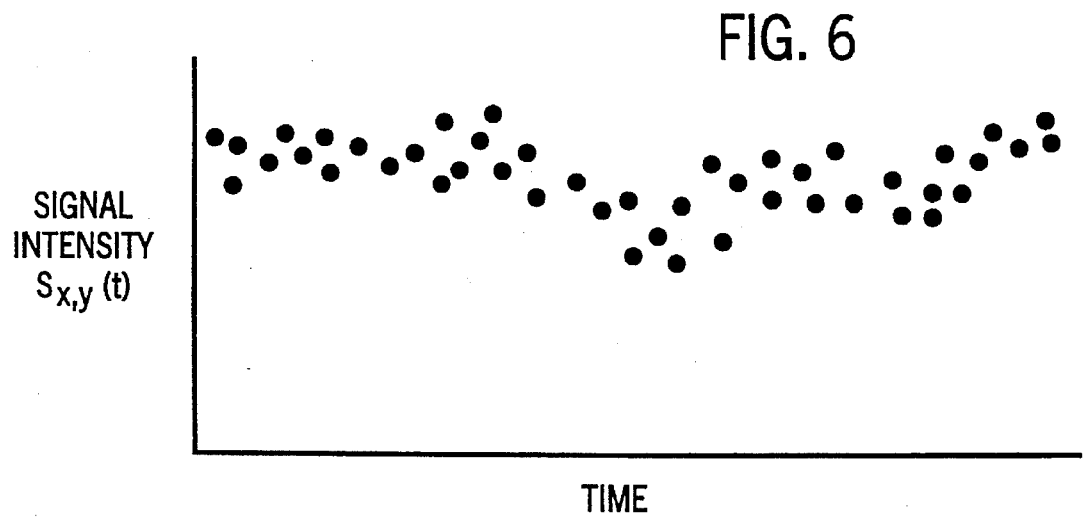
FIG. 6 is a graphic representation of a time course NMR signal from one voxel location in the set of NMR image data of FIG. 5.

Referring particularly to FIGS. 5 and 6, each pixel in the 64 reconstructed NMR images 301 represents the NMR signal strength S at a particular x,y voxel location in the image slice. The set of 64 NMR signals $S_{xy}$ at a voxel location x,y in the successive images is a time course NMR signal $S_{xy}(t)$ which indicates how the NMR signal strength $S_{xy}$ varies as a function of time. One such time course signal $S_{xy}(t)$ is shown graphically in FIG. 6, and it is readily apparent that the expected dip in signal strength as the bolus of contrast agent transits the voxel x,y is present, but masked by noise and the effects of recirculation.

Referring again to FIG. 4, the first step after the time course NMR images have been acquired is to mask out voxels which lie outside the patient. As indicated at process block 302, this is accomplished by adding together the corresponding voxel values $S_{xy}$ in all 64 images to produce one 256×128 summation image. Each value in the summation image sum is compared with a threshold value. It is set to "1" if it exceeds this threshold and it is set to "0" if it does not. This mask is used in all of the subsequent processing to limit the calculations only to those voxels that lie within the mask and, therefore, within the patient. Total processing time is thus reduced by avoiding unnecessary calculations.

Before blood volume is calculated using the nonlinear regression parameter estimation process, the parameters are set to initial "seed" values which enable the process to rapidly converge to the best estimates. As indicated at process block 304, this is accomplished by first calculating a time course average NMR signal $S_a(t)$. The signal values $S_{xy}$ in each of the 64 images 301 are averaged after masking as described above to form each element of the time course average $S_a(t)$. This time course average $S_a(t)$ is then used to set one of the five initial parameter values, $T_a$. The time course average NMR signal $S_a(t)$ is examined to determine the time, $T_a$, when the bolus of contrast agent first arrives at the slice. This is detected as the time of the first dip in the time course average signal $S_a(t)$. As indicated at process block 305, the NMR signal value for a particular voxel in the first image, $S_{xy}(0)$, or the average value of that voxel in the first few minutes, $S_{xy}(0)$, $S_{xy}(1)$, ... (up to time $T_a$), is used to set an initial value of the parameter $S_0$ for each voxel in the image plane. And finally, the remaining three parameters are set to initial "seed" values

β=0.5
β=0.5
BV=0.01 which have been found experimentally to provide good performance for cerebral imaging. The time course average NMR signal $S_a(t)$ is used to determine a point where effects of recirculating contrast begins to strongly influence the shape of the dip in the NMR signal. This point is identified as the final time used in the nonlinear regression parameter estimation which is discussed next.

After the initial seed parameter values have been estimated, a loop is entered in which the blood volume $BV_{xy}$ at each voxel within the masked image is calculated. As indicated at process block 309, this is accomplished using the seed parameter values, the time course NMR signal $S_{xy}(t)$ at the voxel location x,y, and the above described nonlinear regression parameter estimation method. The program described in the above-cited book, "*Numerical Recipes in C, The Art of Scientific Computing Second Edition*", is used for this purpose, and its disclosure is incorporated herein by reference. The model curve and parameters defined above in equation (6) are inputs to this program and the best estimate of the blood volume value $BV_{xy}$ is produced. A test is then made at decision block 311 to determine if blood volume values $BV_{xy}$ have been calculated at all voxel locations. If so, a 256×128 pixel image depicting the blood volume at each voxel is produced for display at process block 313.

As indicated above, 64 images at eight different slice locations were acquired during the scan and the processing is repeated for each slice location. As indicated by decision block 315, when all eight slices have been processed to produce eight corresponding blood volume images, the system exits at 317 and the operator may display or further process the eight images.

APPENDIX A

Efficient implementation of the nonlinear regression routine requires evaluation of the partial derivatives. These terms were calculated with the use of the symbolic mathematical manipulation program entitled "Mathematica" (Wolfram Research, Champaign, Ill.) along with basic principles of differentiation of composite functions and the chain rule of differentiation. Note that there are many repeated terms in the expressions, an efficient implementation would evaluate these only once and then store them for use in the other expressions.

$$S(t) = S_0 \exp\{-k\, TE\, C(t)\} \qquad [A1]$$

where $$C(t) = \frac{C_0}{\Gamma(\alpha+1)} \beta^{-(\alpha+1)} (t-T_a)^\alpha \exp\left(\frac{-(t-T_a)}{\beta}\right).$$

Using the chain rule of differentiation, $$\frac{\partial S}{\partial \alpha} = -k\, TE\, S_0 \exp\{-k\, TE\, C(t)\} \frac{\partial C}{\partial \alpha} \qquad [A2]$$

where $$\frac{\partial C}{\partial \alpha} = \frac{\beta^{-(\alpha+1)} C_0 \exp\left(\frac{-(t-T_a)}{\beta}\right)(t-T_a)^\alpha \left[\log_e\left(\frac{t-T_a}{\beta}\right) - \psi(\alpha+1)\right]}{\Gamma(\alpha+1)}.$$

The partial derivative with respect to α contains the Digamma or Psi function. This function is discussed in Appendix B.

Similarly, $$\frac{\partial S}{\partial \beta} = -k\, TE\, S_0 \exp\{-k\, TE\, C(t)\} \frac{\partial C}{\partial \beta} \qquad [A3]$$

where

-continued $$\frac{\partial C}{\partial \beta} = \frac{\beta^{-(\alpha+3)} C_0 \exp\left(\frac{-(t-T_a)}{\beta}\right)(t-T_a)^\alpha (t-T_a - \beta(\alpha+1))}{\Gamma(\alpha+1)}.$$

$$\frac{\partial S}{\partial C_0} = -k\, TE\, S_0 \exp\{-k\, TE\, C(t)\} \frac{\partial C}{\partial C_0} \quad [A4]$$

where $$\frac{\partial C}{\partial C_0} = \frac{\beta^{-(\alpha+1)} \exp\left(\frac{-(t-T_a)}{\beta}\right)(t-T_a)^\alpha}{\Gamma(\alpha+1)}.$$

$$\frac{\partial S}{\partial T_a} = -k\, TE\, S_0 \exp\{-k\, TE\, C(t)\} \frac{\partial C}{\partial T_a} \quad [A5]$$

where $$\frac{\partial C}{\partial T_a} = \frac{\beta^{-(\alpha+2)} C_0 \exp\left(\frac{-(t-T_a)}{\beta}\right)(t-T_a)^{\alpha-1}(t-T_a - \beta\alpha)}{\Gamma(\alpha+1)}.$$

Finally, $$\frac{\partial S}{\partial S_0} = \exp\{-k\, TE\, C(t)\}. \quad [A6]$$

APPENDIX B  The Digamma or Psi function arises in the expression for the partial derivative of S(t) with respect to α because of the Γ function in the denominator of C(t).

$$\frac{\partial}{\partial x}\left[\frac{1}{\Gamma(x)}\right] = \frac{-\Gamma(x)'}{\Gamma(x)^2} = \frac{-\psi(x)}{\Gamma(x)} \quad [B1]$$

In this application we are concerned only when $x>0$. When $x>2$ the recurrence formula Eq. [B2], can be used to reduce it to a form with $0<x<2$.

$$\psi(m+x) = \frac{1}{(m-1)+x} + \frac{1}{(m-2)+x} + \ldots + \frac{1}{2+x} + \frac{1}{1+x} + \psi(1+x) \quad [B2]$$

The use of this recurrence formula reduces the problem of numerical evaluation of $\psi(x)$ on the interval $0<x<\infty$ to that of the evaluation on the interval $0<x<2$. The remainder of this discussion will be limited to evaluation of the function in this reduced domain.

For integral values of x, the relation $\psi(1) = -\gamma$, where $\gamma$ is the Euler constant=0.57721 56649 01532 86061, avoids division with a zero denominator in the expressions below.

The $\psi$ function can be written as an infinite sum:

$$\psi(x) = -\gamma + \sum_{n=1}^{\infty} \left[\frac{1}{n} - \frac{1}{n+x+1}\right]. \quad [B3]$$

The value of $\psi(x)$ can be approximated as the truncated sum:

$$\psi(x) = -\gamma + \sum_{n=1}^{N} \left[\frac{1}{n} - \frac{1}{n+x-1}\right] + E(x, N) \quad [B4]$$

where E(x,N) is the error term at x. This approximation can be arbitrarily accurate (neglecting round-off errors) if N is sufficiently large. However, for small N this truncated sum is quite inaccurate.

This infinite sum, and thus the error term, is bounded by the overlying and underlying integrals $$\int_N^\infty \left[\frac{1}{n+1} - \frac{1}{n+x}\right] dn \leq E(x, N) \leq \quad [B5]$$

$$\int_N^\infty \left[\frac{1}{n} - \frac{1}{n+x-1}\right] dn$$

With a change of variable in the first term of this expression, and substitution into the second term, the relation can be rewritten as Eq. B6.

$$\int_{N+1}^\infty \left[\frac{1}{n} - \frac{1}{n+x-1}\right] dn \leq E(x, N) \leq \quad [B6]$$

$$\int_N^{N+1} \left[\frac{1}{n} - \frac{1}{n+x-1}\right] dn +$$

$$\int_{N+1}^\infty \left[\frac{1}{n} - \frac{1}{n+x-1}\right] dn$$

Equation [B4] can be rewritten as $$\psi(x) = -\gamma + \sum_{n=1}^{N}\left[\frac{1}{n} - \frac{1}{n+x-1}\right] + \quad [B7]$$

$$\int_{N+1}^\infty \left[\frac{1}{n} - \frac{1}{n+x-1}\right] dn + F(x, N)$$

where F(x,N) is the new error term, with $F(x,N) < E(x,N)$.

$$0 \leq F(x, N) \leq \int_N^{N+1} \left[\frac{1}{n} - \frac{1}{n+x-1}\right] dn \quad [B8]$$

A first approximation to the value of $\psi$ for small N (i.e. 50–100) can be obtained with the use of Eq. [B9] by neglecting the new error term G(x, N). This is a minimax approach which minimizes the maximal possible error in the approximation.

$$\psi(x) = -\gamma + \sum_{n=1}^{N}\left[\frac{1}{n} - \frac{1}{n+x-1}\right] + \quad [B9]$$

$$\int_{N+1}^\infty \left[\frac{1}{n} - \frac{1}{n+x-1}\right] dn +$$

$$\frac{1}{2} \int_N^{N+1}\left[\frac{1}{n} - \frac{1}{n+x-1}\right] dn + G(x, N)$$

The error term F(x,N) represents the total difference between the overlying and underlying integrals. On each interval, [w,w+1], the difference between the integrals can be approximated as the sum of the area of two right triangles, $P_w$ and $Q_w$.

$$F(x, N) \approx \sum_{w=N}^{\infty} [P_w + Q_w] \quad [B10]$$

where $$P_w = \frac{1}{2}\left[\left(\frac{1}{w+1} - \frac{1}{w+x}\right) - \left(\frac{1}{w+2} - \frac{1}{w+x+1}\right)\right]$$

and $$Q_w = \frac{1}{2}\left[\left(\frac{1}{w} - \frac{1}{w+x-1}\right) - \left(\frac{1}{w+1} - \frac{1}{w+x}\right)\right].$$

$P_w$ is approximately the amount of the error term on the interval [w,w+1] which should be included in the sum, whereas $Q_w$ is the approximate amount of the error term which should not be included in the sum. Thus, the approximate fraction of the error term which should be included in the sum is $\delta_w$.

$$\delta_w = \frac{P_w}{P_w + Q_w} = \frac{w(w+x-1)(2w+x+2)}{2(w+1)(w+x)(2w+x+1)} \quad [B11]$$

The final approximation to the value of the $\psi$ function becomes:

$$\psi(x) \approx -\gamma + \sum_{n=1}^{N}\left[\frac{1}{n} - \frac{1}{n+x-1}\right] + \quad [B12]$$

$$\int_{N+1}^{\infty}\left[\frac{1}{n} - \frac{1}{n+x-1}\right] dn +$$

$$(\lambda\delta_N + (1-\lambda)\delta\infty)\int_{N}^{N+1}\left[\frac{1}{n} - \frac{1}{n+x-1}\right] dn,$$

with $(0 \leq \lambda \leq 1)$.

The parameter $\lambda$ can be arbitrarily set to 0.5, or it can be empirically chosen to optimize accuracy in the ranges of x and N commonly used in the evaluation. Note that as N approaches infinity, $\delta_N$ monotonically approaches ½ from below. For large N the approximation given in Eq. [B12] approaches the approximation given in Eq. [B9] (independent of the value of lambda).

An approximate upper limit of the error in Eq. [B9] can now be given:

$$0 \leq G(x, N) \leq (\delta_\infty - \delta_N)\int_{N}^{N+1}\left[\frac{1}{n} - \frac{1}{n+x-1}\right] dn \quad [B13]$$

(approximate)

In the implementation for the present investigation, the value of N=100 and $\lambda$=0.4466 is used. This value of $\lambda$ was empirically found to produce a good approximation to the Digamma function for N=100, it gives accuracy of at least ten digits beyond the decimal place for an interval at least as large as $1.1 \leq x \leq 1.9$. The accuracy is often much better (a few orders of magnitude with proper choice of $\lambda$) than the maximum size indicated by evaluation of the error term. The accuracy of the implementation can be verified by comparison to tabulated values.

I claim:

1. A method for producing an NMR image which indicates blood volume within a slice in a stationary patient, the steps comprising:

a) acquiring NMR data from the slice for a set of $T_2$ weighted images depicting the patient over a course of time;

b) injecting a susceptibility contrast agent into the patient during the course of time such that the patient's blood transports the susceptibility agent through the slice as the NMR data is being acquired;

c) reconstructing the set of $T_2$ weighted images using the acquired NMR data, each $T_2$ weighted image including an array of NMR signal intensity values $S_{xy}$;

d) calculating a blood volume value BV at a voxel location within the slice by forming a time course NMR signal $S_{xy}(t)$ using the corresponding NMR signal intensity values $S_{xy}$ from successive $T_2$ weighted images and fitting a model curve defined by a set of parameters which include the blood volume BV to the time course NMR signal $S_{xy}(t)$ using a nonlinear regression parameter estimation process;

e) repeating step d) for each voxel location in the NMR image; and f) producing the NMR image using the blood volume values BV calculated in step d).

2. The method as recited in claim 1 in which the model curve is defined as $$S_0 \exp\left\{\frac{-k\,TE\,BV}{\Gamma(\alpha+1)}\beta^{-(\alpha+1)}(t-T_a)^\alpha \exp\left(\frac{-(t-T_a)}{\beta}\right)\right\}$$

where $S_0$, $\beta$, $\alpha$, $T_a$ and BV are the parameters estimated by the nonlinear regression parameter estimation process, t represents time, k is a proportionality constant, TE is echo time of an NMR pulse sequence used to acquire the NMR data and $\Gamma$ represents a gamma function.

3. The method as recited in claim 2 in which seed values of the parameter $S_0$, $\beta$, $\alpha$, $T_a$ and BV are calculated before the model curve is fit to the time course NMR signal $S_{xy}(t)$.

4. The method as recited in claim 3 in which the seed parameter values are calculated by fitting the model curve defined by the parameters to a time course average NMR signal $S_a(t)$ formed by calculating an average NMR signal intensity in each of said acquired $T_2$ weighted images.

5. The method as recited in claim 1 which includes producing a mask that indicates voxels outside the patient, and employing the mask to limit the calculation of blood volume BV to those voxels located within the patient.

* * * * *